United States Patent [19]

McLeod et al.

[11] 4,142,412
[45] Mar. 6, 1979

[54] DOPPLER FLOW METER AND METHOD

[75] Inventors: Francis McLeod, Fort Collins, Colo.; Spencer Silverstein, Ithaca; Robert Kurtz, New York, both of N.Y.

[73] Assignee: Sutures Inc., Coventry, Conn.

[21] Appl. No.: 685,902

[22] Filed: May 12, 1976

[51] Int. Cl.² ............................................. G01F 1/66
[52] U.S. Cl. ............................. 73/194 A; 128/2.05 F; 128/2.05 Z
[58] Field of Search ................ 73/194 A; 128/2.05 F, 128/2.05 Z; 340/3 D, 8 L, 8 FT; 310/9.6

[56] References Cited

U.S. PATENT DOCUMENTS

| 2,770,795 | 11/1956 | Peterson | 73/194 A X |
| 3,028,752 | 4/1962 | Bacon | 73/67.8 R |
| 3,685,348 | 8/1972 | Bottcher et al. | 73/67.8 R |
| 3,703,652 | 11/1972 | Noda | 310/9.6 X |
| 3,766,517 | 10/1973 | Fahrbach | 73/194 A X |
| 3,783,967 | 1/1974 | Apgar | 340/8 FT |
| 3,977,247 | 8/1976 | Hassler | 128/2.05 F X |
| 3,987,673 | 10/1976 | Hansen | 128/2.05 F X |
| 4,067,236 | 1/1978 | Hottinger | 73/194 A |

*Primary Examiner*—Charles A. Ruehl
*Attorney, Agent, or Firm*—Larson, Taylor and Hinds

[57] ABSTRACT

A catheter probe flow meter and method of determining the volume flow of a fluid through a conduit, at least one of the fluid and the conduit having energy-scattering interfaces. The method in one embodiment includes transmitting at least two and receiving at least one or transmitting at least one and receiving at least two sound beams through the fluid, resolving the Doppler vectors into an average velocity vector for each transmitting/receiving combination, and resolving the resolved velocity vectors into their component parts.

24 Claims, 18 Drawing Figures

FIG. 9a

DOPPLER FLOW METER AND METHOD

FIELD OF THE INVENTION

This invention relates generally to apparatus and methods for measuring the flow of energy scattering interfaces within a fluid inside a conduit and more particularly to ultrasonic pulse Doppler apparatus and methods for measuring blood flow in a patient's circulatory system.

DESCRIPTION OF THE PRIOR ART

Ultrasonic Doppler flowmeters for measuring the flow of particulate-containing fluid in a conduit are well known. Examples of such devices adapted for measurement of blood flow in a patient's circulatory system are described in U.S. Pat. Nos. 3,430,625 (McLeod); 3,888,238 (Meindl et al); 3,901,077 (McCarty et al); 3,554,030 (Peronneau); 3,542,014 (Peronneau); 3,827,115 (Bom); and 3,766,517 (Fahrbach). As disclosed in these references, the flowmeter usually includes a catheter for insertion into a blood vessel of the patient.

A disadvantage of these and other prior art devices is that the accuracy of the velocity and lumen cross-sectional area measurements obtained is dependent on the orientation of the catheter with respect to the blood flow axis. All of these previous designs require a fixed orientation or position to measure the size of the lumen or the velocity.

A further disadvantage of the prior art is that either separate, specialized function transducer arrangements are required to measure both velocity and lumen area or sensitive and difficult to-implement measurement techniques must be used in order to measure velocity and lumen area with a single, dual-purpose transducer arrangement.

A further disadvantage of the prior art catheters is their complexity and the consequent difficulty of their manufacture.

SUMMARY OF THE INVENTION

These and other disadvantages of the prior art are overcome by the apparatus and methods of the present Invention. The present method is independent of the orientation and position for the measurement of volume flow.

One embodiment of the invention comprises a method for measuring the velocity of a fluid flowing in a conduit wherein at least one of the fluid and the conduit has energy-scattering interfaces. The method comprises transmitting either at least two sound beams at a predetermined angle with respect to each other through the fluid and detecting at least some of the sound beams reflected by the energy scattering interfaces with at least one receiver or transmitting at least one sound beam and detecting the reflected sound beams with at least two receivers. The corresponding Doppler vector for at least two pairs of transmitted and detected sound beams is combined into an average velocity vector and the two or more resolved average velocity vectors are resolved into their component parts to obtain the effective velocity vector.

A second embodiment of the invention relates to determining the effective cross-sectional area of a conduit having a fluid flowing therethrough wherein at least one of the conduit and the fluid has energy-scattering interfaces. The method uses a means for transmitting a sound beam and a means for detecting at least a component thereof and comprises transmitting at least one sound beam per functional set, and calculating the distance to the wall with Doppler range gating techniques. These steps are repeated for a plurality of functional sets and a geometrical shape is constructed. Then the effective cross-sectional area of the constructed shape is calculated.

BRIEF DESCRIPTION OF THE FIGURES

FIG. 3b is a longitudinal cross-section view of a fourth embodiment of transducers 22.

FIG. 4a is a perspective view of a fifth embodiment of transducers 22.

FIG. 4b is a longitudinal cross-section view of the embodiment of transducers 22 illustrated in FIG. 4a.

FIG. 4c is a transverse cross-section view taken along the lines A—A of the embodiment of transducers 22 illustrated in FIGS. 4a and 4b.

FIG. 5a is a perspective view of a sixth embodiment of transducers 22.

FIG. 5b is a longitudinal cross-section view of the embodiment of transducers 22 illustrated in FIG. 5a.

FIG. 8b is a transverse cross-section view taken along the line A-13 A of the embodiment of transducers 22 illustrated in FIG. 8a.

FIG. 9b is an end view of the embodiment of transducers 22 illustrated in FIG. 9a.

DESCRIPTION OF THE PREFERRED EMBODIMENT

The mathematical starting point for determining flow is the Doppler shift vector equation. This equation is as follows:

$$f = [f_o \overline{V} \cdot (\hat{T} - \hat{R})]/C$$

$f$ = the change in frequency
$f_o$ = the base frequency
$\overline{V}$ = Vector velocity of the fluid
$C$ = Velocity of sound in that media
$\hat{T}$ = unit vector representing the direction of the transmitted sound beam
$\hat{R}$ = Unit vector representing the direction of the received sound beam ($\hat{T}$-$\hat{R}$) = Direction Vector of observed Doppler beam The volume flow through any conduit is the vector dot product of the average velocity vector and a cross-sectional area through which that velocity flows. The present method and apparatus employ techniques for velocity measurement and cross-sectional area determinations which are independent of the orientation and position of the transducers. In order to eliminate the orientation of the transducers from being a factor in the determination of the flow velocity, in one embodiment of the invention two sound beams are used. This is because in this embodiment the field radiation pattern is not sufficiently uniform to allow the use of only one transducer. These sound beams can either be transmitted as two or more separate beams and received on one or more receivers or received as two or more separate beams which have been transmitted by one or more transmitters, such as by the transducers described hereinbelow and shown in FIGS. 2 through 9. Each transducer (or transducers) receives signals from the entire cross-section of the conduit. A range gate is moved out in time from the transducers in order to measure a selected region of the conduit. Conventional apparatus and techniques for transmitting and receiving pulsed sound waves and obtaining pulsed Doppler signals on the one hand, and for using the range-gating technique to selectively provide measurements in a plurality of regions in a conduit, on the other hand, are disclosed for example in the aforementioned Peronneau U.S. Pat. No. 3,554,030 and the following articles, Hottinger & Meindl, "An Ultrasonic Technique for Unambiguous Measurement of Blood Volume Flow"; 174 Ultrasonic Symposium Proceedings, IEEE Cat. No. 74 CHO 896-1SU (Hottinger et al article); and in McLeod, "Multichannel Doppler Techniques", published as Chapter 7 of the Proceedings of the International Symposium on Ultrasonics, Janssen, Beerse, Belgium (1973), respectively. Alternately, the signal received can be processed either sequentially with a single movable gate or in parallel with multiple gates or in combinations thereof. Each measurement is the representation of the average velocity through that sampled region. All of the discrete range-gated velocity measurements are summed into an average velocity measurement by the use of a weighting function. This weighting function is calculated to take into account the radar equation, that is to account for transducer radiation pattern, attenuation losses, and the scattering characteristics of the reflective interface. Conventional apparatus and techniques for calculating the velocity from a received range-gated pulse Doppler signal are disclosed for example in the aforementioned Peronneau ('030) and McLeod patents and in an article by Jorgensen, Campan, Baker, "Physical Characteristics and Mathematical Modelling of the Pulsed Ultrasonic Flowmeter", July 1973 Medical and Biological Engineering 404 (Jorgensen article), the Jorgensen article also disclosing the conventional use of a weighting function to sum the velocity measurements into an average velocity measurement. Simultaneously or sequentially, the other transducer (or sets of transducers) scans the conduit and similarly obtains an average velocity measurement as seen by that transducer or transducers. The rate of scan of the transducers must be sufficiently fast that no appreciable change in velocity takes place during the measurement period. Use of these two velocity vectors allows the resolution of the effective velocity component along the axis of the probe in this case. This is done by taking the sums and differences of the vectors in manner consistent with vector algebra. The mathematical vector resolution of the Doppler signals is conventionally done for example by multiplying the signal by a constant which represents the sine or cosine of the known angle between the receiving transducers and the axis of resolution (e.g., the probe axis) as is disclosed for example in the aforementioned Fahrbach patent and the Hokanson U.S. Pat. No. 3,777,740. The aforementioned Fahrbach patent also discloses apparatus and techniques for taking the sums and differences of the vectors. It should be noted that this effective velocity vector need not be parallel to the probe or to the transducers. This effective velocity vector would be an average velocity vector for the effective cross-sectional area in question, as determined hereinbelow.

The next step in the measurement of flow is to measure an effective diameter or cross-sectional area. One method employs the power returned from a Doppler signal. This power is directly proportional to the size of the sampled volume. If the total sampled region over which this measurement takes place is greater than the cross-sectional area of the conduit and includes the conduit in question, the total uncalibrated cross-sectional area would be determined. This measurement can be done as a single measurement or as a sum of separate measurements. A conventional apparatus and technique for performing a power measurement are disclosed for example in the Hottinger et al article. The uncalibrated area is a function of the probe angle to the conduit wall. This uncalibrated area would also vary with different ultrasonic transducers. To obtain the effective cross-sectional area of the conduit, the uncalibrated area must be calibrated and this can be done by the following method. The power returned from a known region completely within the conduit is measured. In the preferred embodiment this is accomplished by using very close range-gating techniques. This technique simultaneously allows the calibration of each individual transducer for gain and gives the power reflected for a known area (volume) of the fluid. Dividing this new factor into the uncalibrated power area mentioned above gives the *effective cross-sectional area.*

The effective velocity vector and the effective surface area need not necessarily be orthogonal to each other. If they are not orthogonal, the angle between the two vectors must be known so that the dot product can be determined.

Since the effective cross-sectional area is known and calibrated orthogonal to the transducers in the preferred embodiment and the effective velocity vector is known parallel to the axis of the transducers, the flow in the conduit is the product of these factors without any other factors having to be known or calculated.

A second method for determining the cross-sectional area is to range to the wall by the use of multiple sets of transducers. Conventional apparatus and techniques for ranging the wall are disclosed in both the aforementioned Peronneau patents. This can be accomplished with *two or more* or more receivers and *one or more* transmitters or *one or more* receivers with *two or more* transmitters per functional set. In these cases, the low frequency Doppler signals, as returned from the wall, can be used to determine the wall position. The preferred embodiment uses sets of transducers to allow the construction of a radiation pattern orthogonal to the catheter. A surface plane of known dimensions can be constructed from these vectors. Conventional apparatus and techniques for construction of a surface plane orthogonal to the radiation pattern are disclosed in the aforementioned Meindl et al patent. Once this effective cross-sectional area is known then this area can be multiplied by the effective velocity vector to give the volume flow through the conduit. A sufficient number of sets of transducers must be used to sample the wall for any significant irregularities, and for the distance to the wall from the sets of transducers. Construction of one or more planes can now be made from the sets of transducers. The angle that the beams were transmitted and received on are known from the geometry of the probes. Since the wall has been sufficiently illuminated, the vessel shape, position of the catheter and the cross-section can all be determined by known algebraic and geometric techniques such as taught for example in the aforementioned Peronneau patents.

The method of using two or more transducers allows the production of a known radiated field. If a known uniform pattern of radiation could be produced with one transmitter/receiver, it would be sufficient to determine the volume flow in a manner to be described hereinafter.

A phased array is a multiple set of transducers generating or operating within a fixed time relationship to simulate a complex transducer, lens, reflector or field. Conventional apparatus and techniques for generating and using a phased array are disclosed in the aforesaid Bom patent. Once the field has been produced, the techniques for measuring the effective velocity, cross-sectional area and calibrations are as previously described.

Figure 2A:
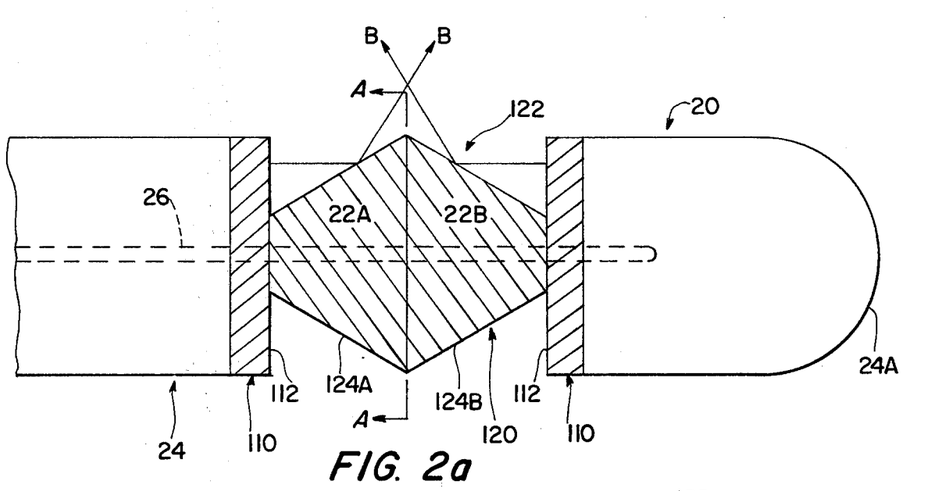
FIG. 2a is a side view, partially in section, of a first embodiment of an intravenous catheter constructed according to the present invention with a first embodiment of transducers 22.
Figure 2B:
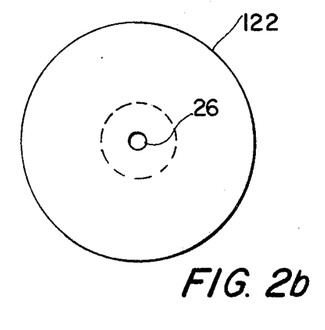
FIG. 2b is a transverse cross-section view of the catheter in FIG. 2a taken along line A-A.

The preferred embodiment is FIG. 2A and 2B. It is to be noted that the methods described herein do not require that one of the exemplary transducer arrangements be utilized. The only requirement for the sound field is that the direction vectors must not be parallel. The direction vector is defined as the vector quantity $(\hat{T}-\hat{R})$.

Several unique characteristics are embodied in the catheters. These are that functional pairs of ultrasonic beams having non parallel Doppler direction vectors can be used for the measurement of velocity. Within this constraint, as stated above, any arrangement of *one or more* transmitters with *two or more* receivers would work as well as *one or more* receivers with *two or more* transmitters. The transmitter/receiver can be a single transducer or multiple transducer.

Another unique feature is a lens or prism to produce a selected field. This lens or prism can be of any material or materials that would refract or bend an ultrasonic signal either received or transmitted. A third unique feature is the use of a reflector. A reflector is any material from which ultrasonic signals would be reflected or be directed as to give the desired angle or field pattern to the beams. The shape of the reflector or reflectors can be varied to give the desired field of radiation or reception. It should be noted that combinations of these effects could be used.

Obviously, the aforementioned concepts can all be adapted extra-luminally. Arrays of two or more transmitters and one or more receivers or two or more receivers and one or more transmitters can be used. A preferred embodiment uses three or more sets of transmitters and one or more receivers or three or more receivers with one or more transmitters. This is done to eliminate the possibility of a misalignment between the conduit and the transducers and therefore possibly erroneous results.

All functional combinations of transducers taken two at a time must radiate in a field pattern which includes the conduit, and the Doppler direction vectors must not be parallel. The techniques for velocity measurement and cross-sectional area determination are all as previously stated.

The single transducer case involves producing a known uniform ultrasonic field to illuminate the total cross-section of the conduit. Conventional apparatus and techniques for generating and using a known uniform ultrasonic field are disclosed for example in the aforesaid Meindl et al patent and the Hottinger et al article. Since the field pattern is defined, velocity measurements can be obtained. The pulse length and sampling period are selected to produce a sampling region normal to the direction of propagation of the sound beam. Under these conditions, the velocity component is everywhere normal to the sampling surface. Integration of the Doppler Frequency over this surface yields a signal, the first moment of which is proportional to the flow. Conventional apparatus and techniques for calculating the integral and the moment are disclosed for example in the Hottinger et al article. Calibration is provided by the same technique as previously described.

For purposes of illustration, an embodiment of a flowmeter constructed according to the present invention which is adapted for measuring blood flow in a patient's circulatory system using an intravenous catheter in the preferred embodiment will now be described.

Figure 1:
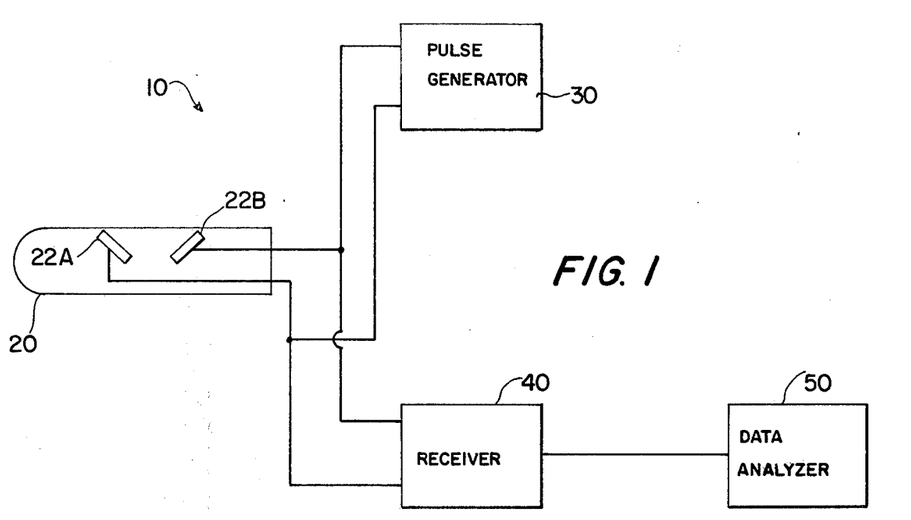
FIG. 1 is a block diagram of a flowmeter constructed according to the pesent invention.

Referring to FIG. 1, the flowmeter, which is generally denoted 10, comprises a catheter 20 having disposed therein first and second transducers, denoted 22A and 22B and referred to collectively as transducers 22, for transmitting and receiving ultrasonic sound waves; generator 30 for pulsing transducers 22; receiver 40 for receiving the signals produced by transducers 22; and data analyzer 50 for determining the blood flow velocity and an effective cross-sectional area of the vessel lumen in the region of measurement.

Referring to FIGS. 2a and 2b, catheter 20 in a first embodiment comprises a catheter housing 24 dimensioned for insertion into a blood vessel of the patient. Transducers 22A and 22B are coaxially disposed in catheter housing 24 on the longitudinal axis of catheter 20. As shown, catheter housing 24 may be tubular and have a blunt tip 24A. A central bore 26 is provided which houses the electrical conductors (not shown) used to connect transducers 22A and 22B with generator 30 and receiver 40.

Figures 6, 7:
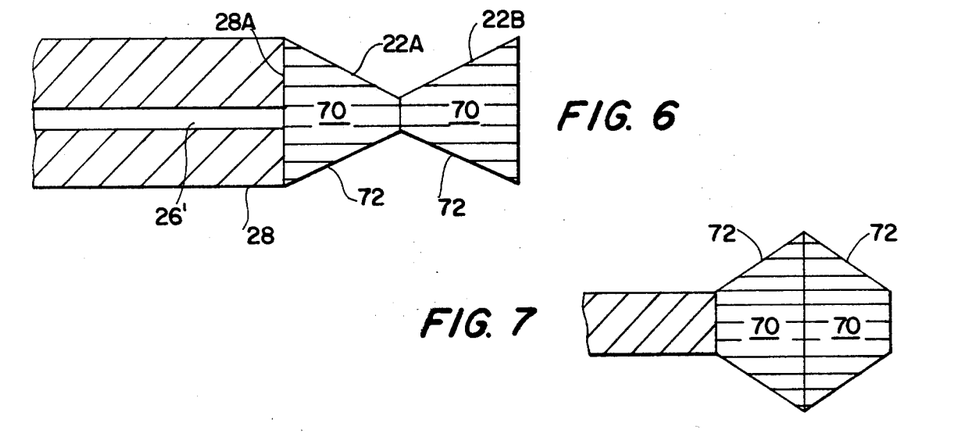
FIG. 6 is a side view, partially in section, of a second embodiment of a catheter constructed according to the present invention having mounted thereon a seventh embodiment of transducers 22.
FIG. 7 is a longitudinal cross-section view of an eighth embodiment of transducers 22.

Referring to FIG. 6, catheter 20 in a second embodiment comprises a support member 28 having a central bore 26' and a base 28A on which transducers 22A and 22B are mounted.

Transducers 22A and 22B are configured and arranged such that first and second beams of ultrasonic sound waves are radiated outwardly at a predetermined angle with respect to each other such that the Doppler vectors representing the sound beams are nonparallel.

Referring to FIGS. 2-9, transducers 22 may comprise a piezoelectric transducer or transducers 110 having transmitting/receiving faces 112 of various configuration, and means 120 for directing the sound waves outwardly from catheter 20 in either converging or diverging directions. In the embodiment of transducers 22 illustrated in FIGS. 2a and 2b, transducers 110 are disposed in spaced substantially coaxial relationship, with planar transducer faces 112 disposed in opposed relationship, facing toward each other, and substantially perpendicular to the axis of catheter 20. As shown in FIG. 2b, transducer faces 112 may have a circular peripheral configuration, or any other peripheral configuration desired. Sound directing means 120 comprises a reflector 122 substantially coaxially disposed between transducers 110. Reflector 122 may have the shape of two back-to-back conical frustrum portions 122A and 122B joined at their enlarged bases, defining two oppositely facing reflecting surfaces 124A and 124B, as shown, The sound beams radiated from transducer faces 112 are thus reflected outwardly from catheter 20.

Figure 2C:
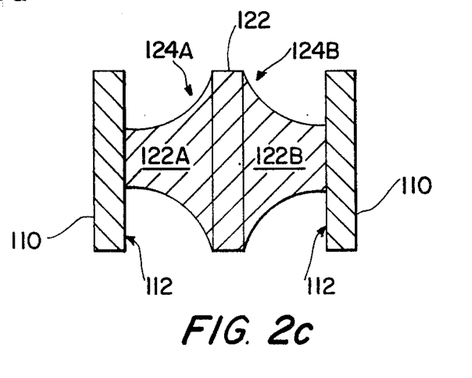
FIG. 2c is a longitudinal cross-section view of a second embodiment of transducers 22.

Reflector 122 may also be shaped such that the reflecting surfaces 124A and 124B of frustrum portions 122A and 122B are curved as viewed in longitudinal cross-section, as shown in FIG. 2c, in order to allow the production of a different ultrasonic field.

Figure 3A:
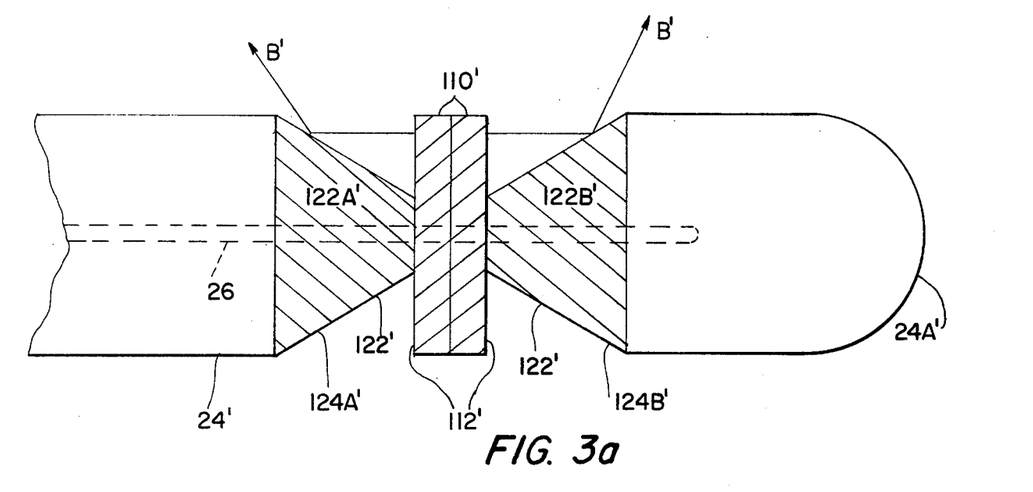
FIG. 3a is a side view, partially in section, of the catheter of FIG. 2a with a third embodiment of transducers 22.

Referring to FIG. 3a, in which elements similar to those of the embodiment of FIGS. 2a and 2b have been given the same reference numbers, with primes attached, transducers 110' are substantially coaxially disposed in juxtaposed, electrically insulated, relationship, such that transducer faces 112 face in opposite directions away from each other. The conical frustrum portions 122A' and 122B' of reflector 122' are spaced, each disposed with the smaller base relatively adjacent the corresponding transducer face, as shown. An embodiment of reflector 122' having curved reflecting surfaces, as viewed in longitudinal cross-section, is shown in FIG. 3b.

Figures 3B, 4A, 4B, 4C:
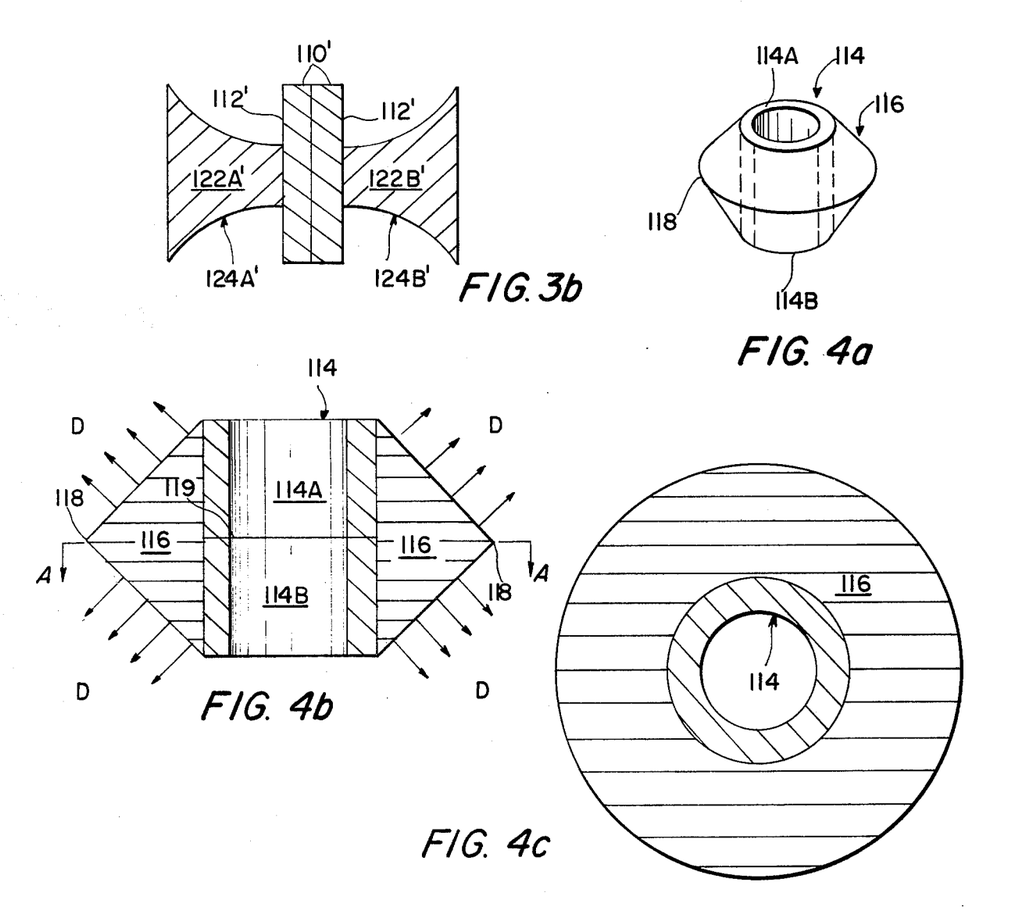

In the embodiment of transducers 22 illustrated in FIGS. 4a to 4c, a single, hollow, cylindrical transducer 114 is transversely divided to form two electrically isolated coaxial portions 114A and 114B, as shown. If a lead-titanate-zirconate (LTZ) piezoelectric transducer is used, both the inner and outer walls thereof are silver coated, and portions 114A and 114B are formed by breaking the silver coating on one or both walls or by assembling two separate substantially coaxially disposed shapes. It is to be noted that transducer 114 may have any desired configuration and need not be in the form of a hollow cylinder.

Surrounding the outer cylindrical surface of transducer 114 is a refracting lens or refractor 116 having the shape of two conical frustrums with a common enlarged base, such that the peripheral configuration defines a triangle, or prism, as viewed in longitudinal cross-section. Refractor 116 is aligned with respect to transducer 114 such that the apex 118 of refractor 116 is in substantially coplanar alignment with the dividing line 110 between transducer portions 114A and 114B. The sound waves radiated outwardly from transducer portions 114A and 114B are thus refracted in diverging or converging directions depending upon the media and the diffractive index of the material, for example as indicated by the arrows D. Refractor 116 may have a laminate construction or utilize a variable density composition to achieve a greater or lesser degree of diffraction.

Figures 5A, 5B:
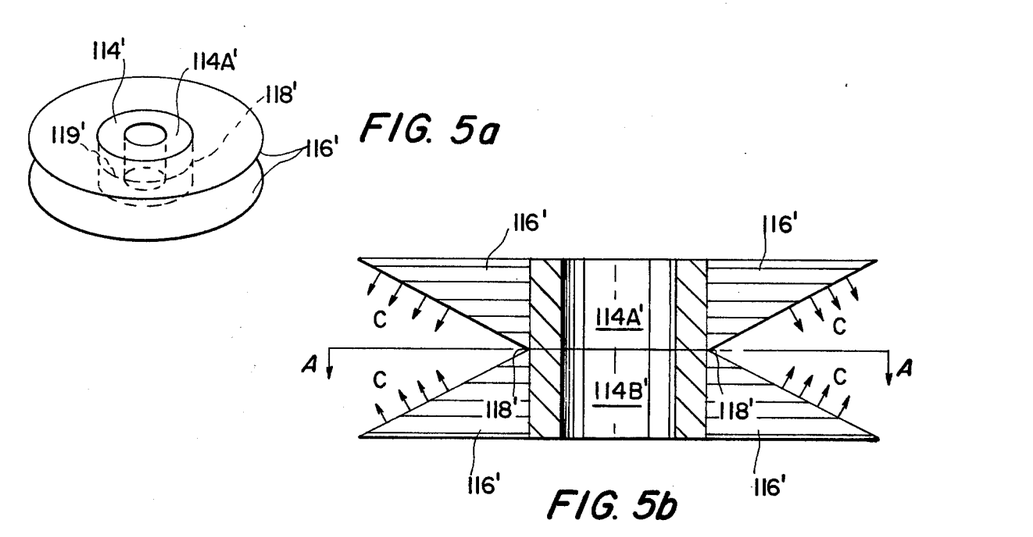
Figure 5C:
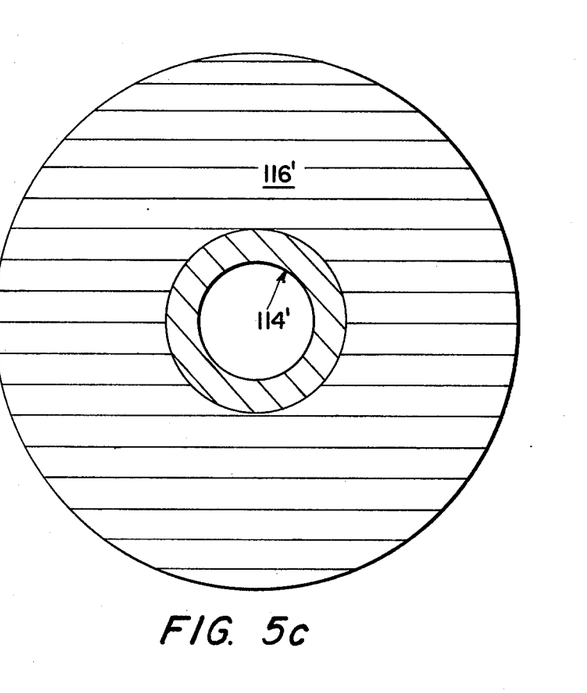
FIG. 5c is a top view of the embodiment of transducers 22 illustrated in FIGS. 5a and 5b.

The embodiment of transducers 22 illustrated in FIGS. 5a to 5c includes elements similar to those of the embodiment of FIGS. 4a to 4c and these elements have been given the same reference numbers, with primes attached. Refractor 116' has a double conical frustrum shape similar to that of refractor 116, except that the frustrum portions are joined at their smaller bases. Refractor 116' is aligned with respect to transducer 114' such that the line of joiner 118' of the two frustrum portions of refractor 116' is in coplanar alignment with the dividing line 119' between crystal portions 114A' and 114B'. The sound waves radiated outwardly from transducer portions 114A' and 114B' are thus refracted in converging or diverging directions, depending upon the media and the refractive index of the material.

With reference to FIGS. 6 and 7, the desired sound beam propagation patterns and directions may also be effected through use of transducers 22A and 22B comprising a piezoelectric transducer or transducers 70 having suitably configured and/or oriented transmitting/receiving faces 72, rather than through use of distinct refracting or reflecting sound directing means. FIGS. 6 and 7 illustrate exemplary embodiments in which transducer 70 are conical, the outer conical surfaces of which define transducers faces 72. The transducers 70 shown in FIG. 6 are so disposed with respect to each other that the respective sound beams radiated therefrom converge, while the transducers 70 shown in FIG. 7 are so disposed that the respective sound beams diverge.

Figure 8:
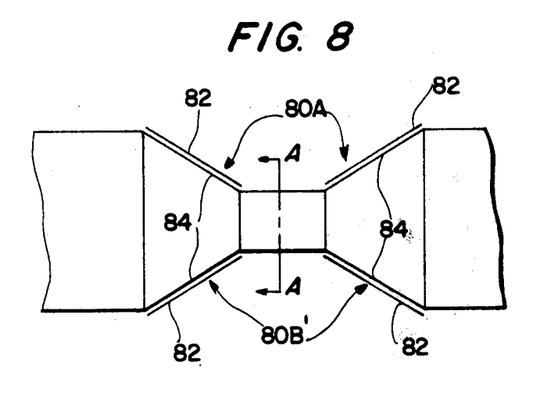
Figure 8A:
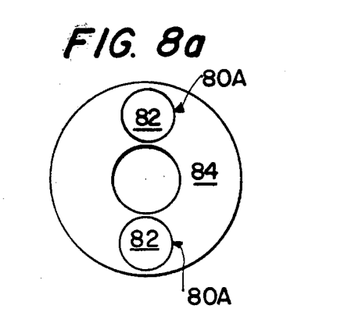
FIG. 8a is a longitudinal cross-section view of a ninth embodiment of transducers 22.
Figure 9:
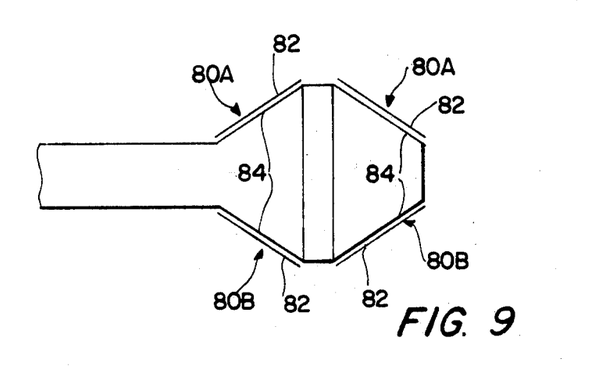
Figure 9A:
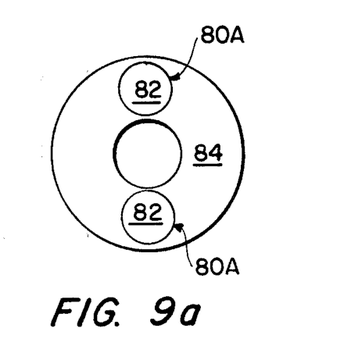
FIG. 9a is a longitudinal cross-section view of a tenth embodiment of transducers 22.

Embodiments of transducers 22 which are advantageously adapted for obtaining "real time" velocity profiles are shown in FIGS. 8 and 9, and comprise first and second pairs of discrete transducers 80A and 80B having transmitting/receiving faces 82 of any desired peripheral configuration and mounted on supporting surfaces 84 which are inclined so as to provide the desired orientations for the respective sound beams radiated from each pair of transducers 80A and 80B.

It is to be noted that the methods to be described hereinbelow do not require that one of the exemplary transducer arrangements described hereinabove be utilized.

Although the invention has been described in detail with respect to exemplary embodiments thereof, it will be understood by those of odinary skill in the art that variations and modifications may be effected within the scope and spirit of the invention.

We claim:

1. A method for measuring the effective velocity of a fluid along a selected axis, the fluid flowing in a conduit, the conduit having one or more regions and the fluid having energy-scattering interfaces, the method comprising the steps of:

transmitting two or more pulsed sound beams at a predetermined angle with respect to each other through the fluid;

detecting at least some of the sound beams reflected by the energy-scattering interfaces in a region in the fluid with one or more receivers, each transmitted pulsed sound beam and each detected sound beam forming a transmitter/receiver group;

repeating the transmitting and receiving steps for each of the one or more fluid regions;

obtaining a Doppler signal which is representative of the velocity vector from each transmitter/receiver group for each region; and in any order combining the one or more Doppler signals for each transmitter/receiver group of each region into a signal representative of the velocity vector for each transmitter/receiver group, resolving the transmitter/receiver group velocity signals into their component parts along the selected axis, and vectorially combining the signals of the transmitter/receiver groups, thereby obtaining the effective velocity vector in said axis.

2. A method for measuring the effective velocity of a fluid flowing through a conduit as claimed in claim 1 comprising the steps of:

transmitting two pulsed sound beams at a predetermined angle with respect to each other through the fluid; detecting at least some of the sound beams reflected by the energy-scattering interfaces with two receivers, the two transmitted sound beams and the two received sound beams forming two transmitter/receiver groups,     combining the one or more Doppler signals into two signals representative of the velocity vectors, one for each transmitter/receiver group; and     resolving and vectorially combining these two velocity signals into their component parts to obtain the effective velocity vector.

3. A method for measuring the effective velocity of a fluid along a selected axis, the fluid flowing in a conduit, the conduit having one or more regions and the fluid having energy scattering interfaces, the method comprising the steps of:

transmitting one or more pulsed sound beams with transmitter means at a predetermind angle thereto through the fluid;

detecting at least some of the sound beams reflected by energy-scattered interfaces in a region in the fluid with two or more receivers, each transmitted pulsed sound beam and each detected sound beam forming a transmitter/receiver group;

repeating the transmitting and receiving steps for each of the one or more fluid regions;

obtaining a Doppler signal which is representative of the velocity vector from each transmitter receiving group for each region; and     in any order, combining the one or more Doppler signals for each transmitter/receiver group of each region into a signal representative of the velocity vector for each transmitter/receiver group, resolving the transmitter/receiver group signals into their component parts along the selected axis, and vectorially combining the signals of the transmitter/receiver groups, thereby obtaining the effective velocity vector in said axis.

4. A method for determining the volume flow of a fluid flowing through a conduit, the conduit having one or more regions along a selected direction and the fluid containing energy-scattering interfaces, wherein the method comprising the steps of:

irradiating the conduit with a pulsed sound radiation field;

receiving with a receiver means sound beams reflected by the energy-scattering interfaces from two, selected directions in said one or more regions in each direction;

determining the effective cross-sectional area of the conduit where the effective cross-sectional area is defined as the cross-sectional area of the conduit taken along any surface which extends completely through the conduit and is independent of the orientation of the receiver to the direction of fluid flow with the steps comprising:

measuring the power returned from the irradiated total cross-sectional area,     range-gating a received signal such that said range-gated signal is returned from a known region totally within the conduit,     measuring the power of this range-gated signal, and     dividing said measured total returned power by said measured range gated power, thereby obtaining said effective cross-sectional area;

determining the effective velocity vector of the fluid flowing through the conduit through said effective cross-sectional area where the effective velocity vector is defined as a vector vectorially combined from resolved representative velocity vectors associated with corresponding said selected directions, and combined from one or more individual velocity vectors, each individual velocity vector representing the velocity of the fluid at an individual region in the effective cross-sectional area, the representative velocity vector being resolved independently of the orientation of the receiver to the direction of fluid flow in a known relationship to said surface, and combined with one or more further individual velocity vectors; and     calculating the volume flow through the conduit by taking the vector dot product of the effective velocity vector and the effective cross-sectional area.

5. A method as claimed in claim 4 for determining the volume flow of a fluid through a conduit wherein said conduit is irradiated by an array of transducers operating within a fixed time relationship as a phased array.

6. A method for using a plurality of transducers as a phased array of transducers operating within a fixed time relationship to simulate a complex transducer for determining the effective velocity of a fluid along a selected axis, the fluid flowing through a conduit having a plurality of regions and at least the fluid containing energy-scattering interfaces, whereby the method comprises:

transmitting pulsed sound beams from the phased array through the fluid;

detecting with said phased array at least some of the sound beams reflected by the energy-scattering interfaces in a region of the fluid in at least two directions from said array;

repeating the transmitting and detecting steps for each of the fluid regions;

determining a Doppler signal for each region;

combining the Doppler signals into at least two signals representative of a velocity vector, each signal corresponding to a direction; and     resolving these at least two velocity signals into their component parts about said axis and vectorially combining said component parts, thereby obtaining the effective velocity vector.

7. A method for determining the volume flow of a fluid flowing through a conduit, the conduit having at least one region and the fluid containing energy-scattering interfaces, wherein the method comprises:

irradiating the conduit with 'm' pulsed sound beams at a predetermined angle with respect to each other through the fluid;

receiving from each region a sound beam reflected by the energy-scattering interfaces with 'n' receivers, each transmitted sound beam and each receiver forming a transmitter/receiver group;

where 'm' and 'n' are integers equal to or greater than 1 and selected so as to provide at least two transmitter/receiver groups;

determining an effective cross-sectional area of the conduit where the effective cross-sectional area is defined as the area of the conduit taken along a surface which transects the conduit and which is independent of the orientation of said transmitter/receiver group to the direction of fluid flow;

determining the effective velocity vector of the flowing fluid through said effective cross-sectional area where the effective velocity vector is defined as a vector combined vectorially from a plurality of transmitter/receiver group velocity vectors, each group velocity vector being a resolved representative velocity vector of, the representative velocity vector being resolved in a known relationship to said surface;

calculating the volume flow through the conduit by taking the vector dot product of the effective velocity vector and the effective cross-sectional area.

8. A method for determining the volume flow of a fluid flowing through a conduit, the conduit having at least one region and the fluid containing energy-scattering interfaces, wherein the method comprises:

irradiating the conduit with 'm' pulsed sound beams at a predetermined angle with respect to each other through the fluid;

receiving from each region a sound beam reflected by the energy-scattering interfaces with 'n' receivers, each transmitted sound beam and receiver forming a transmitter/receiver group;

where 'm' and 'n' are integers equal to or greater than 1 and selected so as to provide at least two transmitter/receiver groups;

determining an effective cross-sectional area of the conduit where the effective cross-sectional area is defined as the area of the conduit taken along a surface which transects the conduit and which is independent of the orientation of the transmitter/receiver group to the direction of fluid flow;

determining the effective velocity of the flowing fluid through said effective cross-sectional area by:

obtaining a Doppler signal from each transmitter/receiver group for each region; and in any order combining the Doppler signal for each transmitter/receiver group of each region into a signal representative of the velocity vector for each transmitter/receiver group, resolving the plurality of transmitter/receiver group velocity signals into their component parts about an axis which intersects said surface at a known angle, and combining vectorially the signals of the transmitter/receiver groups, thereby obtaining said effective velocity vector about said axis;

and calculating the volume flow through the conduit by taking the vector dot product of the effective velocity vector and the effective cross-sectional area.

9. The method as claimed in claim 8 wherein said 'm' irradiating sound beams are irradiated by 'm' transmitters and wherein said 'm' transmitters and said 'n' receivers are mounted in a probe along said axis.

10. The method as claimed in claim 9 wherein said probe is included in a catheter and said method further comprises initially inserting said catheter into a blood vessel of a patient.

11. A method for determining the volume flow of a fluid flowing through a conduit, the conduit having at least one region and the fluid containing energy-scattering interfaces, wherein the method comprises:

irradiating the conduit with 'm' pulsed sound beams at a predetermined angle with respect to each other through the fluid;

receiving from each region a sound beam reflected by the energy-scattering interfaces with 'n' receivers, each transmitted sound beam and receiver forming a transmitter/receiver group;

where 'm' and 'n' are integers equal to or greater than 1 and selected so as to provide at least two transmitter/receiver groups;

determining an effective cross-sectional area of the conduit where the effective cross-sectional area is defined as the area of the conduit taken along a surface which transects the conduit and which is independent of the orientation of the transmitter/receiver group to the direction of fluid flow;

determining the effective velocity of the flowing fluid through said effective cross-sectional area by:

obtaining a Doppler signal from each transmitter/receiver group for each region; and in any order combining the Doppler signal for each transmitter/receiver group of each region into a signal representative of the velocity vector for each transmitter/receiver group, wherein said representative velocity signal is obtained by multiplying each individual velocity signal with a weighting function and summing the weighted individual velocity signals, resolving the plurality of transmitter/receiver group velocity signals into their component parts about an axis which intersects said surface at a known angle, and combining vectorially the signals of the transmitter/receiver groups, thereby obtaining said effective velocity vector about said axis;

and calculating the volume flow through the conduit by taking the vector dot product of the effective velocity vector and the effective cross-sectional area.

12. A method for determining the volume flow of a fluid flowing through a conduit, the conduit having a plurality of regions and the fluid containing energy-scattering interfaces, wherein the method comprises:

irradiating the conduit with 'm' pulsed sound beams at a predetermined angle with respect to each other through the fluid;

receiving from each region a sound beam reflected by the energy-scattering interfaces with 'n' receivers, each transmitted sound beam and receiver forming a transmitter/receiver group;

where 'm' and 'n' are integers equal to or greater than 1 and selected so as to provide at least two transmitter/receiver groups, said 'm' sound beams and 'n' receivers forming a first functional set;

irradiating the conduit with 'i' pulsed sound beams at a predetermined angle with respect to each other through the fluid;

receiving from each region a sound beam reflected by the energy-scattering interfaces with 'j' receivers, each transmitted sound beam and receiver forming a transmitter/receiver group;

where 'i' and 'j' are integers equal to or greater than 1 and selected so as to provide at least two transmitter/receiver groups, said 'i' sound beams and 'j' receivers forming a second functional set;

determining an effective cross-sectional area of the conduit as follows:

detecting the sound beams reflected from the walls of the conduit with said at least two transmitter/receiver groups of said first functional set;

calculating the distance to the walls from the detected sound beams using Doppler range gating techniques;

repeating the above detecting and calculating steps for said second functional set;

constructing a geometrical surface from said calculated distances to the wall obtained from each functional set; and calculating the area of said surface, said area being the effective cross-sectional area;

determining the effective velocity vector of the flowing fluid through said effective cross-sectional area where the effective velocity vector is defined as a vector combined vectorially from a plurality of transmitter/receiver group velocity vectors, each group velocity vector being a combined and resolved representative velocity vector of at least one individual velocity vector, each individual velocity vector representing the velocity of the fluid at an individual region in the effective cross-sectional area, the representative velocity vector being resolved in a known relationship to said surface;

and calculating the volume flow through the conduit by taking the vector dot product of the effective velocity vector and the effective cross-sectional area.

13. The method as claimed in claim 12 wherein said transmitters and receivers of said first and second functional sets are operated as an array of transducers.

14. A method for determining the volume flow of a fluid flowing through a conduit, the conduit having at least one region and the fluid containing energy-scattering interfaces, wherein the method comprises:

irradiating the conduit with 'm' pulsed sound beams at a predetermined angle with respect to each other through the fluid; at receiving from each region a sound beam reflected by the energy-scattering interfaces with 'n' receivers, each transmitted sound beam and receiver forming a transmitter/receiver group;

where 'm' and 'n' are integers equal to or greater than 1 and selected so as to provide a6t least two transmitter/receiver groups;

determining an effective cross-sectional area of the conduit which is independent of the orientation of the transmitter/receiver group to the direction of fluid flow as follows:

transmitting a sound beam through the fluid such that the total sound radiation pattern includes a total cross-sectional area of the conduit;

detecting at least some of the reflected sound beams and calculating the Doppler signal therewith;

determining the total power of the calculated Doppler signal, the total power being representative of the uncalibrated area of the conduit;

detecting at least a part of a sound beam which is reflected only from a selected volume that is entirely contained within the conduit and calculating the Doppler signal therewith;

measuring the power return from said selected volume Doppler signal thereby obtaining a calibration factor; and dividing the determined total power by the calibration factor to obtain the effective cross-sectional area of the conduit;

determining the effective velocity vector of the fluid through said effective cross-sectional area of the conduit where the effective velocity vector is defined as a vector combined vectorially from a plurality of transmitter/receiver group velocity vectors, each group velocity vector being the resolved average velocity vector of a plurality of individual velocity vectors, each individual velocity vector representing the velocity of the fluid at an individual region in the effective cross-sectional area, the average velocity vector being resolved in a known relationship to a predetermined axis;

calculating the volume flow through the conduit by taking the vector dot product of the effective velocity vector and the effective cross-sectional area.

15. A method for determining the volume flow of a fluid flowing through a conduit, the conduit having at least one region and the fluid containing energy-scattering interfaces, wherein the method comprises:

irradiating the conduit with 'm' pulsed sound beams at a predetermined angle with respect to each other through the fluid;

receiving from each region a sound beam reflected by the energy-scattering interfaces with 'n' receivers, each transmitted sound beam and each receiver forming a transmitter/receiver group;

where 'm' and 'n' are integers equal to or greater than 1 and selected so as to provide at least two transmitter/receiver groups;

determining an effective cross-sectional area of the conduit which is independent of the orientation of the transmitter receiver groups to the direction of the fluid flow as follows:

transmitting a sound beam through the fluid such that the total sound radiation pattern includes the total cross-sectional area of the conduit;

detecting at least some of the reflected sound beams and calculating the Doppler signal therewith;

determining the total power of the calculated Doppler signal, the total power being representative of the uncalibrated area of the conduit;

detecting at least a part of a sound beam which is reflected only from a selected volume that is entirely contained within the conduit and calculating the Doppler signal therewith;

measuring the power return from said selected volume Doppler signal thereby obtaining a calibration factor; and dividing the determined total power by the calibration factor to obtain the effective cross-sectional area of the conduit;

determining the effective velocity vector of the fluid through said effective cross-sectional area of the conduit by:

obtaining a Doppler signal from each transmitter/receiver group for each region; and in any order combining the plurality of Doppler signals for each transmitter/receiver group of each region into a representative velocity vector for each transmitter/receiver group, resolving the plurality of transmitter/receiver group representative velocity signals into their component parts about an axis which intersects said effective area at a known angle and which is independent of the orientation of the transmitter/receiver group to the direction of the fluid flow, and combining vectorially the signals of the transmitter/receiver groups, thereby obtaining said effective velocity vector about said axis;

and calculating the volume flow through the conduit by taking the vector dot product of the effective velocity vector and the effective cross-sectional area.

16. A method for determining the volume flow of a fluid flowing through a conduit, the conduit having at least one region and the fluid containing energy-scattering interfaces, wherein the method comprises:
  irradiating the conduit with a pulsed sound beam generated by a phased array of transducers comprising a plurality of transducers operating within a fixed time relationship to simulate a complex transducer such that the total radiation pattern includes a total cross-sectional area of the conduit;
  receiving from each region with said phased array at least some of the sound beams reflected by the energy-scattering interfaces in that region;
  calculating a Doppler signal with the received sound beams from each region;
  determining the total power return to the receivers of the Doppler signal;
  scanning with said phased array a known volume that is entirely contained within the conduit;
  determining the power return of the calculated Doppler signal from the scanned volume, said power being defined as the calibration factor for the transducers and sound beams of the array and the fluid;
  obtaining the effective cross-sectional area of the conduit by dividing the total power return by the calibration factor;
  determining the effective velocity vector of the fluid through said effective cross-sectional area of the conduit where the effective velocity vector is defined as the resolved combined velocity vector of a plurality of individual velocity vectors, each individual velocity vector representing the velocity of the fluid at an individual region in the effective cross-sectional area, the average velocity vector being resolved in a known relationship to said axis;
  calculating the volume flow through the conduit by taking the vector dot product of the effective velocity vector and the effective cross-sectional area.

17. A method for measuring the effective velocity of a fluid along a selected axis, the fluid flowing in a conduit, the conduit having a plurality of regions and the fluid having energy-scattering interfaces, the method comprising the steps of:
  transmitting two or more pulsed sounds beams at a predetermined angle with respect to each other through the fluid;
  detecting at least some of the sound beams reflected by the energy-scattering interfaces in a region in the fluid with one or more receivers, each transmitted pulsed sound beam and each detected sound beam forming a transmitter/receiver group;
  repeating the transmitting and receiving steps for each region;
  obtaining a Doppler signal which is representative of the velocity vector from each transmitter/receiver group for each region; and
  in any order combining the one or more Doppler signals for each transmitter/receiver group of each region into a signal representative of the velocity vector for each transmitter/receiver group, resolving the transmitter/receiver group velocity signals into their component parts along the selected axis, and combining vectorially the signals of the transmitter/receiver groups, thereby obtaining the effective velocity vector in said axis.

18. A method for measuring the effective velocity of a fluid along a selected axis, the fluid flowing in a conduit, the conduit having a plurality of regions and the fluid having energy-scattering interfaces, the method comprising the steps of:
  transmitting one or more pulsed sound beams at a predetermined angle or angles through the fluid;
  detecting at least some of the sound beams reflected by energy-scattering interfaces in a region in the fluid with two or more receivers, each transmitted pulsed sound beam and each detected sound beam forming a transmitter/receiver group;
  repeating the transmitting and receiving steps for each region;
  obtaining a Doppler signal which is representative of the velocity vector from each transmitter/receiver group for each region; and
  in any order, combining the one or more Doppler signals for each transmitter/receiver group of each region into a signal representative of the velocity vector for each transmitter/receiver group, resolving the transmitter/receiver group velocity vectors into their component parts along the selected axis, and combining vectorially the signals of the transmitter/receiver groups, thereby obtaining the effective velocity vector in said axis.

19. A method for determining the volume flow of a fluid flowing through a conduit, the conduit having a plurality of regions and the fluid containing energy-scattering interfaces, wherein the method comprises the steps of:
  irradiating the conduit with a pulsed sound radiation field from a transmitter;
  receiving with a receiver means sound beams reflected by the energy-scattering interfaces in said regions;
  determining the effective cross-sectional area of the conduit where the effective cross-sectional area is defined as the cross-sectional area of the conduit taken along any surface which extends completely through the conduit and is independent of the orientation of the receiver to the direction of fluid flow;
  determining the effective velocity vector of the fluid flowing through the conduit through said effective cross-sectional area where the effective velocity vector is defined as a vector combined vectorially from a plurality of group velocity vectors, one group velocity vector being associated with each different direction from which a sound beam is received and the group velocity vectors each representing a combined and resolved velocity vector of individual velocity vectors, each individual velocity vector representing the velocity of the fluid at an individual region in the effective cross-sectional area, the group velocity vector being resolved independently of the orientation of the receiver to the direction of fluid flow and in a known relationship to said surface; and
  calculating the volume flow through the conduit by taking the vector dot product of the effective velocity vector and the effective cross-sectional area.

20. A method for determining the volume flow of a fluid flowing through a conduit, the conduit having a plurality of regions and the fluid containing energy-scattering interfaces, wherein the method comprises:

irradiating the conduit with 'm' pulsed sound beams at a predetermined angle with respect to each other through the fluid;

receiving from each region a sound beam reflected by the energy-scattering interfaces with 'n' receivers, each transmitted sound beam and each receiver forming a transmitter/receiver group;

where 'm' and 'n' are integers equal to or greater than 1 and selected so as to provide at least two transmitter/receiver groups;

determining an effective cross-sectional area of the conduit where the effective cross-sectional area is defined as the area of the conduit taken along a surface which transects the conduit and which is independent of the orientation of said transmitter/receiver group to the direction of fluid flow;

determining the effective velocity vector of the flowing fluid through said effective cross-sectional area where the effective velocity vector is defined as a vector combined vectorially from a plurality of transmitter/receiver group velocity vectors, each group velocity vector being a combined and resolved representative velocity vector of a plurality of individual velocity vectors, each individual velocity vector representing the velocity of the fluid through an individual region in the effective cross-sectional area, the representative velocity vector being resolved in a known relationship to said surface;

calculating the volume flow through the conduit by taking the vector dot product of the effective velocity vector and the effective cross-sectional area.

21. A method for determining the volume flow of a fluid flowing through a conduit, the conduit having a plurality of regions and the fluid containing energy-scattering interfaces, wherein the method comprises:

irradiating the conduit with 'm' pulsed sound beams at a predetermined angle with respect to each other through the fluid;

receiving from each region a sound beam reflected by the energy-scattering interfaces with 'n' receivers, each transmitted sound beam and receiver forming a transmitter/receiver group;

where 'm' and 'n' are integers equal to or greater than 1 and selected so as to provide at least two transmitter/receiver groups;

determining an effective cross-sectional area of the conduit where the effective cross-sectional area is defined as the area of the conduit taken along a surface which transects the conduit and which is independent of the orientation of the transmitter/receiver group to the direction of fluid flow;

determining the effective velocity of the flowing fluid through said effective cross-sectional area by:

obtaining a Doppler signal from each transmitter/receiver group for each region; and in any order combining the plurality of Doppler signals for each transmitter/receiver group of each region into a signal representative of the combined velocity vector for each transmitter/receiver group, resolving the plurality of transmitter/receiver group velocity signals into their component parts about an axis which intersects said surface at a known angle, and combining vectorially the signals of the transmitter/receiver groups, thereby obtaining said effective velocity vector about said axis;

and calculating the volume flow through the conduit by taking the vector dot product of the effective velocity vector and the effective cross-sectional area.

22. The method as claimed in claim 21 wherein said 'm' irradiating sound beams are irradiated by 'm' transmitters and wherein said 'm' transmitters and said 'n' receivers are mounted in a probe along said axis.

23. A method as claimed in claim 21 wherein said combined velocity vector is obtained by multiplying each individual velocity signal with a weighting function and summing the weighted individual velocity signals.

24. A method for determining the volume flow of a fluid flowing through a conduit, the conduit having a plurality of regions and the fluid containing energy-scattering interfaces, wherein the method comprises:

irradiating the conduit with 'm' pulsed sound beams at a predetermined angle with respect to each other through the fluid;

receiving from each region a sound beam reflected by the energy-scattering interfaces with 'n' receivers, each transmitted sound beam and each receiver forming a transmitter/receiver group;

where 'm' and 'n' are integers equal to or greater than 1 and selected so as to provide at least two transmitter/receiver groups;

determining an effective cross-sectional area of the conduit which is independent of the orientation of the transmitter/receiver groups to the direction of the fluid flow as follows:

transmitting a sound beam through the fluid such that the total sound radiation pattern includes the total cross-sectional area of the conduit;

detecting at least some of the reflected sound beams and calculating the Doppler signal therewith;

determining the total power of the calculated Doppler signal, the total power being representative of the uncalibrated area of the conduit;

detecting at least a part of a sound beam which is reflected only from a selected volume that is entirely contained within the conduit and calculating the Doppler signal therewith;

measuring the power return from said selected volume Doppler signal thereby obtaining a calibration factor; and dividing the determined total power by the calibration factor to obtain the effective cross-sectional area of the conduit; determining the effective velocity vector of the fluid through said effective cross-sectional area of the conduit by:

obtaining a Doppler signal from each transmitter/receiver group for each region; and in any order combining the plurality of Doppler signals for each transmitrer/receiver group into a representative velocity signal for each transmitter/receiver group, resolving the plurality of transmitter/receiver group velocity signals into their component parts about an axis which intersects said effective area at a known angle and which is independent of the orientation of the transmitter/receiver group to the direction of the fluid flow, and combining vectorially the signals of the transmitter/receiver groups, thereby obtaining said effective velocity vector about said axis; and calculating the volume flow through the conduit by taking the vector dot product of the effective velocity vector and the effective cross-sectional area.

* * * * *